United States Patent [19]

Hölzl

[11] Patent Number: 4,581,934
[45] Date of Patent: Apr. 15, 1986

[54] METHOD OF AND APPARATUS FOR MEASUREMENT OF THE GAS LOADING OF A LIQUID SYNTHETIC-RESIN COMPONENT

[75] Inventor: Emil Hölzl, Munich, Fed. Rep. of Germany

[73] Assignee: Krauss-Maffei Aktiengesellschaft, Munich, Fed. Rep. of Germany

[21] Appl. No.: 610,017

[22] Filed: May 14, 1984

[30] Foreign Application Priority Data

May 13, 1983 [DE] Fed. Rep. of Germany ....... 3317486

[51] Int. Cl.$^4$ ............................................. G01N 9/02
[52] U.S. Cl. ........................................ 73/438; 73/19
[58] Field of Search .................. 73/19, 433, 434, 438, 73/439; 137/3, 88, 91; 264/40.1, 50

[56] References Cited

U.S. PATENT DOCUMENTS

| | | | |
|---|---|---|---|
| 2,541,102 | 2/1951 | Rymal | 73/438 |
| 3,690,184 | 9/1972 | Chadenson | 73/438 |
| 4,089,206 | 5/1978 | Raffel et al. | 73/19 |
| 4,195,527 | 4/1980 | Ebeling | 73/434 |
| 4,201,082 | 5/1980 | Dockhorn | 73/438 |
| 4,365,505 | 12/1982 | Holzl | 73/19 |

FOREIGN PATENT DOCUMENTS

| | | |
|---|---|---|
| 2724132 | 11/1978 | Fed. Rep. of Germany . |
| 2723618 | 11/1978 | Fed. Rep. of Germany . |
| 3030779 | 3/1982 | Fed. Rep. of Germany . |

Primary Examiner—Stewart J. Levy
Assistant Examiner—Robert R. Raevis
Attorney, Agent, or Firm—Karl F. Ross; Herbert Dubno

[57] ABSTRACT

A method of and an apparatus for the measurement of the degree of gas charging of a liquid component of a foam synthetic resin such as a polyurethane. The gas-charged liquid component is introduced into a measuring vessel to a height controlled by an overflow so as to be fixed. The degree of charging is then determined from the measured hydrostatic pressure of each column.

11 Claims, 1 Drawing Figure

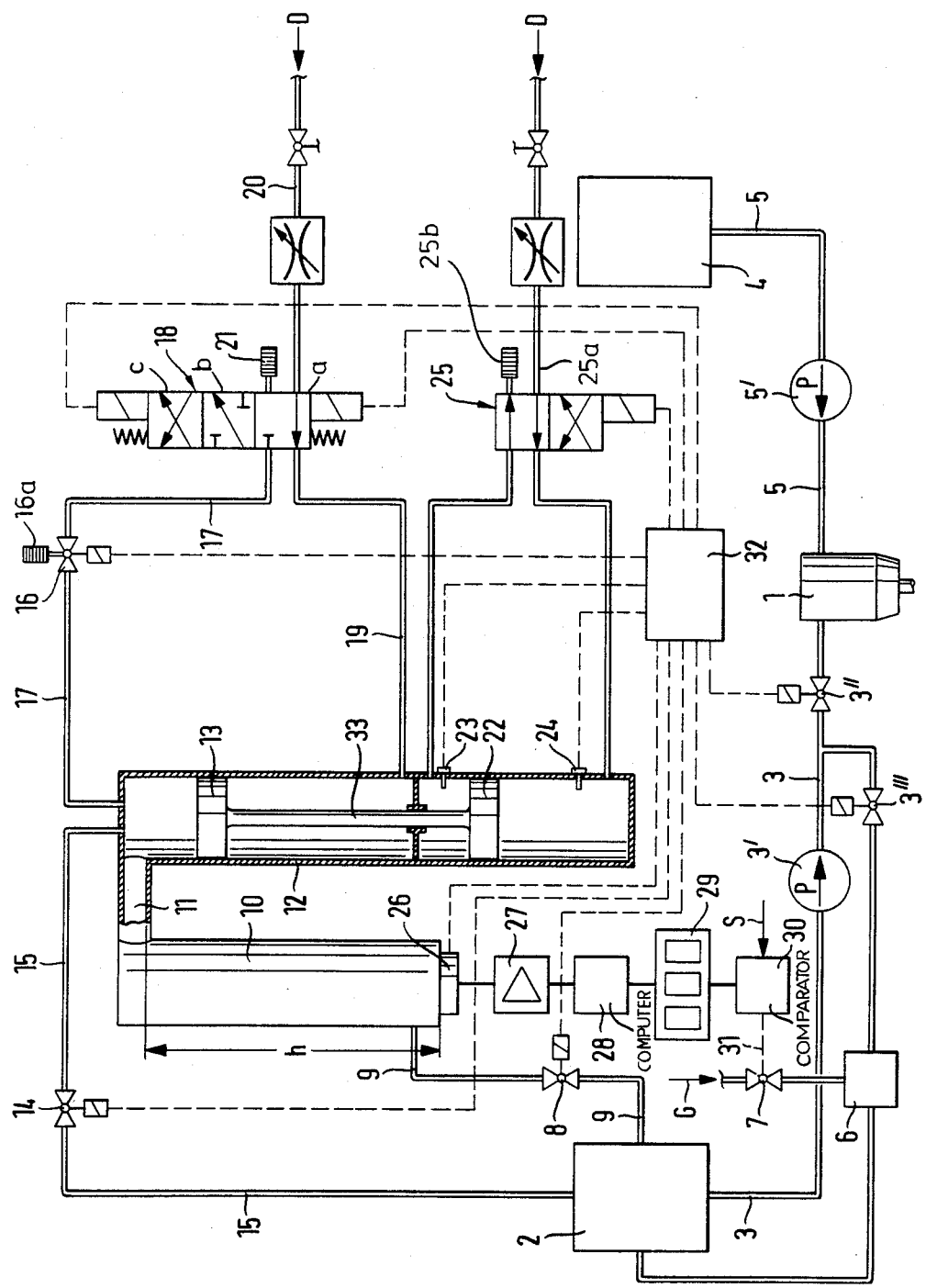

METHOD OF AND APPARATUS FOR MEASUREMENT OF THE GAS LOADING OF A LIQUID SYNTHETIC-RESIN COMPONENT

FIELD OF THE INVENTION

My present invention relates to a method of and to an apparatus for the measurement of the charge of a gas contained in a liquid synthetic-resin component and, more particularly to the measurement of the gas loading of foamable synthetic-resin components, especially a component adapted to react to form a polyurethane foam.

BACKGROUND OF THE INVENTION

In the production of foamed, cellular or expanded synthetic resins, e.g. foamed polyurethane, it is known to incorporate a gas in the synthetic-resin mixture and to permit expansion of the gas with setting of the product so that the latter will have a cellular, reticulate or foamed conformation.

One way of incorporating a gas in the reaction mixture, of course, is to charge one of the liquid components of the reaction system with the gas under pressure or by some other means.

The degree to which this component has been charged with the gas is a reflection on the nature of the quality of the product and thus it is desirable from time to time to measure the gas charge introduced into or the gas loading of a liquid synthetic resin component.

In U.S. Pat. No. 4,089,206, there is described a method of and an apparatus for measuring the proportion of undissolved gas in a liquid component for the production of foam materials in which the sample of liquid component is periodically diverted from the tank containing same into a measuring vessel.

In this system, the measuring vessel is in effect a decompression chamber and the measurement is carried out by determining the rise in a liquid column as a result of its decompression.

Measurement in this fashion is particularly slow and awkward since the decompression of the liquid column is a comparatively slow process. Furthermore, the accuracy of the process is poor when the liquid component is also provided with a solid charge of reinforcing or extending solid particles such as glass fibers. One of the problems with the measurement precision is that the variable level to which the decompression chamber is filled cannot be readily detected by the eye and can only be controlled with the requisite precision and speed with complex and extensive means. Furthermore, with this system, it is only possible to obtain relative values of the density and not an absolute value which is frequently necessary.

OBJECTS OF THE INVENTION

It is, therefore, the principle object of the present invention to provide a method of measuring the undissolved gas content of a liquid component of a synthetic resin which has greater precision and can be carried out more rapidly than the earlier systems so that quasi-continuous measurements of this parameter can be made.

Still another object of the invention is to provide an improved method of determining the gas content of a liquid synthetic-resin component which can provide an absolute measurement rather than the relative measurements obtained heretofore.

A further object of this invention is to provide an improved method of and apparatus for the measurement of the gas loading of a liquid synthetic-resin component whereby the disadvantages of earlier systems are obviated.

It is also an object of this invention to provide an improved apparatus for the purposes described which can effect a substantially automatic and quasi-continuous determination of the degree to which a liquid synthetic-resin component is charged with gas.

SUMMARY OF THE INVENTION

These objects and others which will become apparent hereinafter are attained, in accordance with the present invention in a method for measuring the gas loading of a liquid synthetic-resin component under the system pressure of a foam synthetic-resin molding system, especially a system for the molding of polyurethane foams, wherein at periodically spaced intervals a sample from a tank of the liquid component is diverted to a measuring vessel. According to the invention, within the measuring vessel a constant height of the liquid component charged with the gas is established and the hydrostatic pressure of this liquid column is determined as a measurement of the density of the gas-charged synthetic-resin component.

The method of the invention can be carried out with high precision and speed so that fluctuations in the degree of charging of the synthetic-resin component with the gas can be minimized when such charging is manually or automatically controlled in response to the measurement obtained. This ensures the production of synthetic-resin articles of substantially constant quality.

In apparatus terms, a system for carrying out the measurement of the present invention will generally include a measuring vessel adapted to receive a column of the gas-charged liquid synthetic-resin component, means for measuring the hydrostatic pressure of this column, means preferably including an overflow for automatically establishing a constant height of the column and means responsive to the hydrostatic pressure measurement for calculating the absolute density of the gas-charged liquid component and making any necessary calculations of the charge of gas therein. Utilizing the overflow to establish the height of the column, it is possible to fix the column height rapidly and with a minimum instrumentation and control cost and hence with maximum efficiency. Indeed, since the overflow height-control system works rapidly, it is possible to carry out the measurements at extremely short measurement separation intervals, thereby permitting the measurements to be quasi-continuous.

In the preferred embodiment of the invention, the overflow extends into an overflow vessel or compartment whose volume is variable by means of a piston. The piston in turn is actuated by a valve system and the measuring vessel can be provided with an inlet valve whereas the overflow vessel can have an outlet valve. The measuring vessel can also have a venting valve which can be opened to allow filling thereof and a control unit can be provided for the above mentioned valves and the piston and can be controlled in accordance with a predetermined program, e.g. via a microprocessor. The programming allows automatic sampling and measurement and also variation of the volume of the overflow vessel.

At the bottom of the measurement vessel a pressure sensor is preferably disposed and means can be provided for compensating in the measurement for variations in atmospheric pressure. The calculator can be provided with a memory or other data storage enabling empirically determined standardization data and/or physical law data and physical characteristics of the components and the gas to be introduced so that the computer can carry out the requisite mathematical calculations and analyses to establish the density and gas content of the gas-charged liquid component even before a significant expansion phase has occurred.

The control system may also include a delay for the opening of the vent valve so that when the intake and discharge valves are closed, the descent of the piston can accelerate the expansion phase by applying a pressure reduction to the liquid column.

Since the device compensates for variations in the atmospheric pressure and/or allows measurements which take into consideration the atmospheric pressure, it is possible to establish the gas loading parameter under the conditions of greatest interest, e.g. as where the synthetic resin components are to be processed at atmospheric pressure or atmospheric pressure is to prevail in the foaming mold or in the other parts of the apparatus.

Preferably the hydrostatic pressure-measuring unit is a Bourdon gauge communicating with the bottom of the measuring cylinder through the bottom wall or through a lateral wall thereof.

BRIEF DESCRIPTION OF THE DRAWING

The above and other objects, features and advantages of the present invention will become more readily apparent from the following description, reference being made to the accompanying drawing in which the sole FIGURE is a diagram in partial section and partially in block or flow-diagram form of an apparatus for carrying out the method of this invention.

SPECIFIC DESCRIPTION

With reference to the drawing, it can be seen that a polyurethane foam-molding installation can have a mixing head 1 to which the liquid components are fed in the form of a polyol and isocyanate for intimate mixture and discharge into a mold. The mixing head has been shown in a simplified form and can include a recirculation system for separating two components when a plunger is displaced into the mixing chamber and enabling recirculation of the components to the respective tanks.

Accordingly, the system can also comprise a polyol tank 2 from which the liquid polyol component is delivered via a polyol line 3 and a polyol pump 3' to the mixing head 1. The isocyanate tank 4 is connected by the isocyanate line 5 and the isocyanate pump 5' to the mixing head 1.

The polyol line 3 is provided with control valves 3" and 3"40 , the latter connecting this line with a gas-charging unit 6. In the unit 6, a portion of the polyol can be subjected to pressurization with the foaming or blowing gas which can be supplied via a gas line provided with a valve 7 as represented by arrow G under the control of a gas-control valve.

The gas-charged polyol is returned to the tank 2.

To briefly clarify this gas-charging operation, it may be noted that the valve 3" can be closed, the valve 3"' opened, the valve 7 opened to a controlled extent and the pump 3 operated to circulate the liquid polyol from the tank 2 via the pump 3', the pressurization unit 6 and back to the tank. By controlling the rate of this recirculation and the valve 7, it is possible to maintain a given degree of charging of the liquid polyol synthetic-resin component with the blowing gas.

From the tank 2 under the control of a sampling valve or inlet valve 8, a sampling or branching line 9 can divert samples of the liquid polyol to a measuring vessel or cylinder 10.

The cylinder 10 is connected by an overflow 11 at its upper end to an overflow vessel 12 whose volume can be varied by the displacement of a piston 13. A discharge valve 14 is connected to the overflow chamber and returns the polyol component after measurement via line 15 to the tank 2.

The overflow vessel 12 is also provided with a controllable venting valve 16 in a compressed-air line 17 running to a four-port, three-position valve (4/3 distributing valve) 18. The three positions of this valve can be designated a,b, and c, respectively.

A further pressure line 19 is connected to the 4/3 valve 18 and extends to the lower end of the cylinder formed by the overflow vessel 12 in which the piston 13 is received.

Two of the four ports of the valve 18 are connected to the line 17 and 19, respectively, while the remaining two ports are connected to a compressed-air line 20 and to a vent 21 provided with a sound muffler 21.

The piston 13 is provided with a position-detecting piston 22 cooperating with a pair of sensors 23 and 24 and controllable in accordance with servomechanism practices by a four-port, two-position (4/2) valve 25 having a compressed air-source 25a, a venting muffler 25b and an actuator responsive to the microprocessor controller 32.

At the bottom of the measuring cylinder or vessel 10, I provide a pressure sensor 26 which can be a Bourdon gauge, a piezo electric pressure-sensitive element or a strain-gauge pressure detector.

The pressure sensor 26 is connected via an amplifier (27) to a calculator or computer (28) which can have a storage or memory containing the requisite parameters for the calculations described and a display 29 whose alphanumeric output can provide a direct display of the degree of loading of the liquid component with the gas or an equivalent parameter such as the absolute density of the gas-charged liquid component.

The computer can also have an output representing an actual value of the degree of gas charging of the liquid component which is applied to a comparator 30 receiving a set-point value S and generating an output signal 31 which is utilized to control the valve 7 directly so that the degree of charging can be adjusted in accordance with the measured value so as to maintain the degree of charging constant.

The piston 13 can, as has been illustrated, be displaced or controlled as to its position from either or both of two devices, namely the valve 18 and the valve 25.

The inlet valve 8, the valves 3" and 3"', the discharge valve 14, the venting valve 16 which is provided with a muffler 16a, and the valves 18 and 25 controlling the piston 13 are, together with the sensors 23 and 24 and the pressure sensor 26, connected to the control unit 32 which is advantageously a microprocessor-controlled programmer adapted to carry out the sequencing of the apparatus as described below:

A. Filling and flushing of the measuring cylinder 10.

In the upper deadpoint position of the piston 13, as signalled led to the controller 32 by the sensor 23, the intake valve 8 is opened and the discharge valve 14 and the venting valve 16 are closed. By switching the 4/3 valve 18 into its position b, the region below the piston 13 is vented and under the system pressure prevalent in the tank 2, the liquid polyol flows via line 9 into the measuring cylinder 10, thereby driving the piston 13 downwardly until the piston reaches its lower deadpoint position as signalled by the sensor 24. The controller is thus signalled to close the valve 8 and to open the discharge valve 14. The 4/3 valve 18 is shifted into position a and the underside of the piston 13 is pressurized with compressed air to displace this piston 13 upwardly. The polyol which is overflowed into the vessel 12 is thereby displaced via line 15 back to the tank. The process is repeated until there has been complete replacement of any previous polyol in the measuring cylinder 10.

The filling and flushing operation can also be carried out utilizing the piston 22 and the valve 25 for self-sufficient displacement of the piston without requiring the pressure from the tank 2.

B. Measurement of the gas loading of the liquid synthetic-resin component.

Once the liquid component, i.e. the polyol, for the new sample has replaced any sample for the polyol in the measuring cylinder 10, the controller 32 signals the beginning of a measuring operation. The measuring operation begins with the piston 13 in its upper deadpoint position with closure of the intake valve 8 and the discharge valve 14. The valve 18 is shifted to position c by the controller 32 and the piston 13 is driven downwardly by compressed air. The venting valve 16 is then open so that atmospheric pressure prevails in the overflow vessel and the gas-charged synthetic-resin component can thus expand from the system pressure to atmospheric pressure and overflow through the outlet 11 which always defines a constant height h of the liquid column contained in the measuring cylinder 10.

After termination of the expansion phase, which can generally take two to three minutes and can be controlled by a time-delay circuit or program of the controller 32, the density measurement is effected by the pressure sensor 26. The density $\rho$ of the liquid column has the following relationship with respect to the height of the column:

$$\rho = p/h \cdot g$$

In this relationship p is the hydrostatic pressure and g the acceleration of gravity. Since the values of h and g are constant, the density of the liquid column is directly proportional to the hydrostatic pressure p.

The pressure value is thus amplified at 27 and supplied to the display 29 either as an absolute density or as the degree of gas loading, a comparison of the absolute density being made in the computer 28 with empirically derived data representing the relationship between the absolute density and the gas loading of the particular polyol component or a collection of liquid synthetic-resin components which can be selected by entering appropriate data into the computer.

The feed-back control of the degree of gas loading via the comparator 30 has already been described.

The measurement process can be accelerated at comparatively little cost by switching on the pressure sensor 26 at the beginning of the expansion phase provided, of course, that the empirically derived data of the computer 28 has been obtained in such manner as to take into consideration the short expansion phase or the absence of an expansion phase in generating the readout. In other words the computor can interpolate from the empirical data to the reading in the expanded condition without necessarily waiting for the full expansion. In this way I can reduce the spacing between measurement intervals without having to wait for the full expansion period described and, for example, density measurement can be taken at intervals of 15 to 30 seconds.

It is also possible to accelerate the measuring process by, after the start of the measuring process and with the valves 8 and 14 closed, driving the piston 13 downwardly via the piston 22 and the control valve 25. The valve 18 is here in position b and the downward forcing of the piston 13 can apply a reduced pressure to the vessel 12 and in the measuring vessel 10 for a period which can accelerate the expansion, e.g. for about 0.5 minutes. In this manner the expansion step which would otherwise have taken say three minutes can be reduced to about ½ minute. The duration of this evacuation step can be effected by providing the venting valve 16 with a time-constant circuit, e.g. within the controller 32.

The invention thus permits highly accurate measurement of the gas charge of a liquid synthetic-resin component, for example the polyol so that the measurements are highly reproducible and can be utilized to maintain the degree of charging of the gas constant within very narrow ranges. This is important to maintaining the quality of the synthetic-resin end products.

I claim:

1. A method of measuring the degree of charging of a liquid synthetic-resin component for the production of a foam synthetic resin with a gas which comprises the steps of:
    (a) periodically withdrawing samples of a gas-charged liquid synthetic-resin component from a tank containing same under a system pressure;
    (b) feeding said samples in succession to a measuring vessel constructed and arranged to repetitively and reproducibly establish a liquid column therein of a constant height h for said samples by effecting overflow of said samples above said height;
    (c) detecting the hydrostatic pressure of said columns; and
    (d) indicating a parameter representing the degree of gas charging of each of said samples as a function of the hydrostatic pressure p of each of said columns of said height h.

2. The method defined in claim 1, further comprising the step of controlling the charging of said liquid component with said gas by comparing said parameter with a set-point value and regulating the contact of said gas with said liquid component in response to said comparison.

3. An apparatus for measuring the degree of charging of a liquid synthetic-resin component for the production of a foam synthetic resin with a gas, which comprises:
    an upright measuring vessel provided at an upper location thereof with an overflow for establishing a constant height h of liquid columns of respective liquid samples delivered to said vessel;
    means for drawing said samples from a tank containing a liquid synthetic-resin charged with gas under a system pressure and introducing said samples into said vessel;
    a hydrostatic pressure sensor on said vessel responsive to the hydrostatic pressure p of said columns; and means connected to said sensor for indicating a parameter p proportional to the absolute density of said samples and to the degree of charging thereof with gas.

4. An apparatus for measuring the degree of charging of a liquid synthetic-resin component for the production of a foam synthetic resin with a gas, which comprises:

an upright measuring vessel provided at an upper location thereof with an overflow for establishing a constant height h of liquid columns of respective liquid samples delivered to said vessel;

means for drawing said samples from a tank containing a liquid synthetic-resin charged with gas under a system pressure and introducing said sample into said vessel;

a hydrostatic pressure sensor on said vessel responsive to the hydrostatic pressure p of said columns;

means connected to said sensor for indicating a parameter proportional to the absolute density of said samples and to the degree of charging thereof with gas;

an overflow vessel connected to the overflow of said measuring vessel and receiving overflow of said liquid component therefrom;

a piston in said overflow vessel displaceable to vary the effective volume thereof;

means for displacing said piston in said overflow vessel;

an intake valve connected between said tank and said measuring vessel;

a discharge valve connected between said overflow vessel and said tank for returning overflow liquid component to said tank upon advance of said piston;

a vent valve communicating with said measuring vessel to apply atmospheric pressure to the contents thereof; and a control unit connected to said valves and to said sensor for the programmed operation of said valves to effect filling and flushing of said measuring vessel in each sample and measurement of the hydrostatic pressure thereof.

5. The apparatus defined in claim 4, further comprising:

a pump connected to said tank for delivering said liquid component to a mixing head;

a first valve connected between said pump and said mixing head;

a gas-charging unit connected to said pump and said tank;

second valve connected between said pump and said unit; and means connecting said first and said second valve to said controller for controlling the circulation of said liquid component through said unit.

6. The apparatus defined in claim 5, further comprising means responsive to said parameter for comparing same with a set-point value to control the degree of charging of said components with gas in said unit.

7. The apparatus defined in claim 5 wherein means is provided for compensating for the effect on said parameter of fluctuations in atmospheric pressure above said liquid columns.

8. The apparatus defined in claim 5, further comprising circuit means connected to said sensor for evaluating the hydrostatic pressure detected therein and producing the indication of said parameter.

9. The apparatus defined in claim 8 wherein said circuit means includes preprogrammed empirical data which is compared with the detected hydrostatic pressure to provide an output representing density or gas content of said liquid component.

10. The apparatus defined in claim 8 wherein said circuit includes means for calculating said parameter in accordance with a preprogrammed mathematical function representing a physical law relating said parameter to hydrostatic pressure.

11. The apparatus defined in claim 5, further comprising delay means connected to said venting valve for delaying the opening thereof so that an opposite movement of said piston applies a vacuum to a liquid column in said measuring vessel.

* * * * *